US00PP35135P2

(12) United States Plant Patent
Hansen

(10) Patent No.: US PP35,135 P2
(45) Date of Patent: Apr. 25, 2023

(54) ***HOSTA* PLANT NAMED 'GIGANTOSAURUS'**

(50) Latin Name: ***Hosta* hybrid**
Varietal Denomination: Gigantosaurus

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,734

(22) Filed: Nov. 1, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02
See application file for complete search history.

*Primary Examiner* — Kent L Bell

(57) ABSTRACT

A new and distinct *Hosta* plant named 'Gigantosaurus' with large, rounded-mound habit of heavy-substance, stiff, variegated foliage. Leaves are moderately glaucous, broadly ovate with coarsely, weakly-undulate, creamy-white margins, bluish-green centers and intermediate colors between. Flowers are light purple, held just above foliage beginning in late June. The new plant is attractive for landscaping in the garden as a specimen, in mass and as a large container plant.

2 Drawing Sheets

Botanical classification: *Hosta* hybrid.
Variety denomination: 'Gigantosaurus'.

STATEMENT REGARDING PRIOR DISCLOSURES UNDER 37 CFR 1.77(b)(6)

*Hosta* 'Gigantosaurus' was first introduced by the inventor as a non-enabling description through the International Cultivar Registration Authority registration in early 2021. No plants of *Hosta* 'Gigantosaurus' have been sold, in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Gigantosaurus' hereinafter also referred to as the new plant or by the cultivar name, 'Gigantosaurus'. *Hosta* 'Gigantosaurus' was a single seedling selection from a cross on Jun. 14, 2012, by the inventor at a wholesale perennial nursery in Zeeland, Mich., USA between the non-patented, unreleased, proprietary, unnamed, streaked-variegated, sport selected from 'Empress Wu' U.S. Plant Pat. No. 20,774 as the female parent and 'Blueberry Muffin' (non-patented) as the male parent. The new plant was assigned the breeder code 12-83-16 and passed the initial evaluation in the summer of 2016. The new plant has been asexually propagated by division at the same nursery in Zeeland, Mich., USA since 2017 and also by careful plant shoot-tip tissue culture with the resultant asexually propagated plants having retained all the same traits as the original plant. *Hosta* 'Gigantosaurus' has been stable and reproduces true to type plants in successive generations of asexual reproduction.

BRIEF SUMMARY OF THE PLANT

There are over 7,000 registered and established *Hosta* cultivars recognized by The American *Hosta* Society, which is the International Cultivar Registration Authority for the genus *Hosta*. The nearest comparison cultivars known to the inventor are: *Hosta* 'Northern Exposure' (not patented), 'Terms of Endearment' U.S. Plant Pat. No. 34,806, 'Hope Springs Eternal' U.S. Plant Pat. No. 33,266, 'Sugar Daddy' (not patented), and 'Wu-La-La' U.S. Plant Pat. No. 31,309.

All of the above plants have a green to bluish-green center and a cream-yellow to white variegated margin. 'Northern Exposure' has a smaller habit but with more rounded and bullate leaves and the flowers are near white. 'Terms of Endearment' has leaf margins that start the spring more chartreuse and mature to creamy-yellow, and the flowers are pale purple to near white. 'Hope Springs Eternal' has a smaller habit and smaller foliage with a more acute apex, and more undulation in the margins, and the flowers are medium lavender on scapes reaching further above the foliage. 'Sugar Daddy' has a smaller habit and leaf size, the leaves are more rounded and bullate, and the margin is more yellowish. 'Wu-La-La' has foliage that is less glaucous, the margin is more yellowish and the scapes are much taller and produce wider spaced flowers of pale purple subtended by larger bracts.

The female parent has leaves that are irregularly streaked creamy white and deep green in a mericlinal chimera pattern and has a larger habit with larger leaves and the flowers are lighter lavender compared to the new plant. The male parent has rounder, more bluish leaves without variegation.

Other *Hosta* cultivars may have similar colored variegated foliage, but 'Gigantosaurus' is distinct from the above-listed *Hostas* and all other cultivars known to the inventor by the following combined traits:

1. Large-sized, round-mounded plant habit with heavy-substance, stiff foliage;
2. Moderately glaucous leaves are broadly ovate with weakly and coarsely undulate margin;
3. Leaf margins are creamy-white and centers are bluish-green with intermediate colors between;

4. Medium-sized flowers are on strongly upwardly projecting scapes just above foliage;
5. Tepals are light purple with slightly darker veins and translucent margins.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color. The drawings show a nine-year-old 'Gigantosaurus' plant in a trial garden at a nursery in Zeeland, Mich. with supplemental fertilizer and water as needed.

DETAILED BOTANICAL DESCRIPTION

Figure 1:
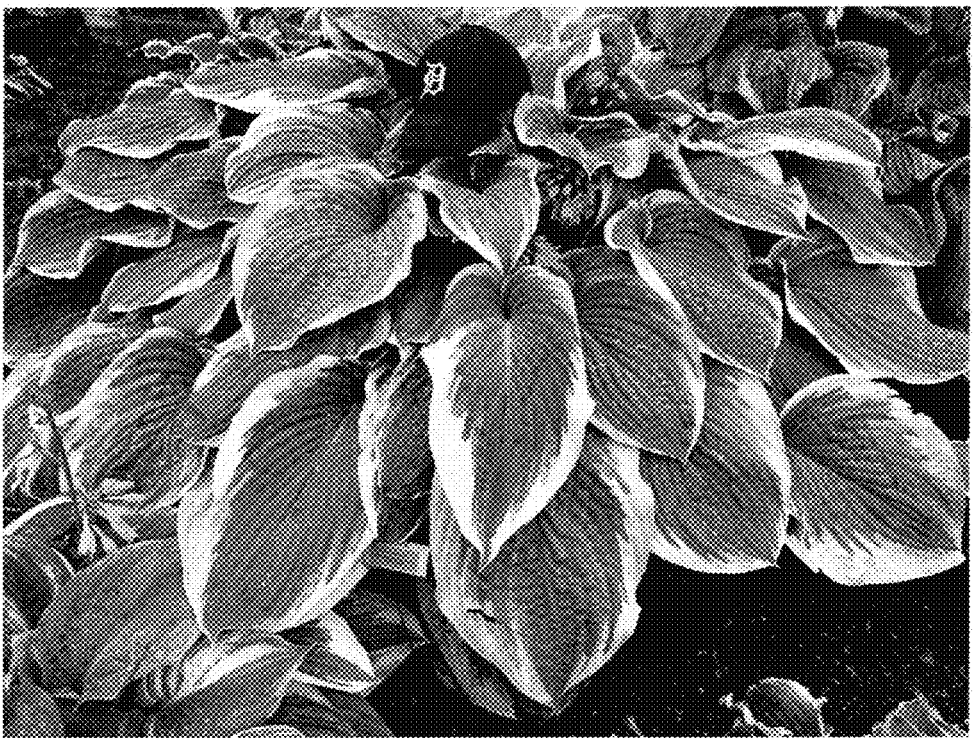
FIG. 1 shows the habit of a nine-year-old plant with early flowers and buds.
Figure 2:
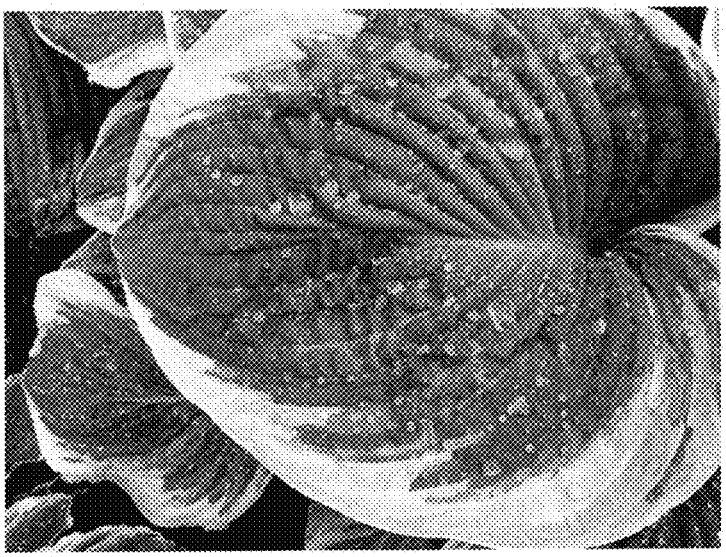
FIG. 2 shows a close-up of the foliage with variegation.
Figure 3:
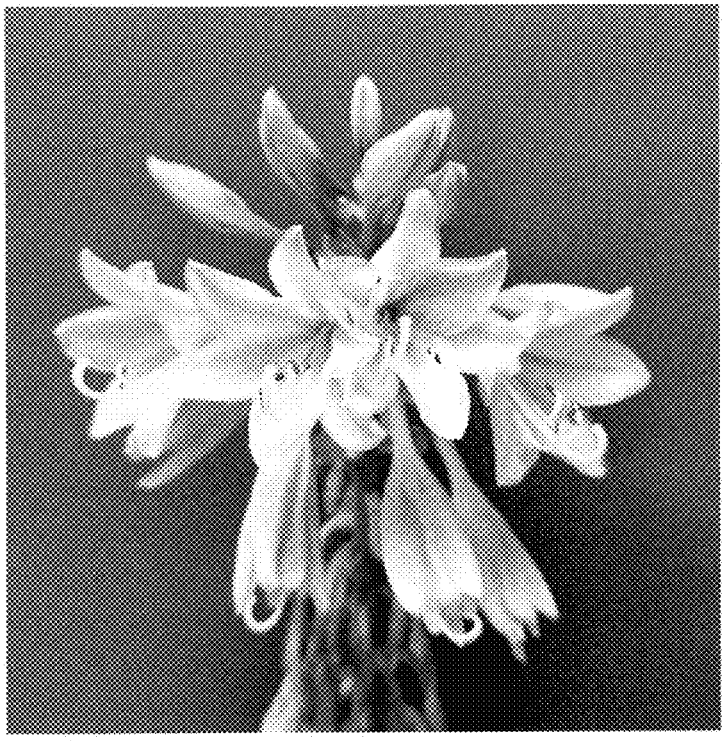
FIG. 3 shows a close-up of the flowers.

The following descriptions and color references are based on the 2015 edition of The Royal Horticultural Society Colour Chart except where common dictionary terms are used. The new plant, *Hosta* 'Gigantosaurus' has not been observed under all possible environments. The phenotype may vary slightly with different environmental conditions, such as temperature, light, fertility, moisture and maturity levels, but without any change in the genotype. The following observations and size descriptions are of a nine-year-old plant in a partially shaded trial garden in Zeeland, Mich. with supplemental water and fertilizer.

Botanical classification: *Hosta* hybrid.

Parentage: A proprietary unnamed streaked-variegated sport of 'Empress Wu' as the female parent and 'Blueberry Muffin' as the male parent.

Propagation: Garden division and sterile shoot-tip tissue culture.

Time to initiate roots from tissue culture: About two to three weeks.

Growth rate: Rapid.

Crop time: About 10 to 12 weeks to finish during the summer in a one-liter container from rooted tissue culture plantlet.

Rooting habit: Normal, fleshy, lightly branching; color between RHS NN155A and RHS NN155B depending on soil content.

Plant shape and habit: Hardy herbaceous perennial with basal rosettes of leaves emerging from rhizomes producing a large, symmetrical, rounded-mound of leaves; about 12 divisions per plant; divisions to about 3 cm diameter at soil level.

Plant size: Foliage height about 77 cm above soil line to the top of the leaves and about 193 cm wide at the widest point about 30 cm above the soil line.

Foliage description: Broadly ovate; acute apex; cordate base; entire margin; glabrous and moderately glaucous adaxial, and glabrous and moderately glaucous abaxial; blades mostly flat with coarse, weakly undulate margin; with a thick stiff feel.

Leaf blade size: To about 42.5 cm long, 29 cm wide at base; average about 36 cm long and 25 cm wide; with variegated cream-white margin of variable width between 1 cm and 4.5 cm wide.

Leaf blade color: Early season and expanding adaxial margin between RHS 145C and RHS 1C, adaxial center nearest RHS 137B with intermediate colors comprising nearest RHS N144D, RHS 146B, RHS 145A and between RHS 193B and RHS 145C; early season and expanding abaxial margin nearest RHS 145C and center between RHS 138B and RHS 138A with intermediate colors comprising RHS 146D, and between RHS 193B and RHS 147D; mid-season and later summer adaxial margin nearest RHS 155A in light shade and between RHS 150C and RHS 145C in heavy shade or underneath other foliage, center nearest RHS 137B, intermediate region variable comprising RHS 146C, RHS N138B, between RHS 148D and RHS 190B, between RHS 145D and RHS 146D; mid-season and later summer abaxial margin variable, nearest RHS 155A in higher light, and nearest RHS 4D to nearest RHS 145D in heavy shade or underneath other foliage, center nearest RHS 138B with glaucous covering removed and between RHS 191C and RHS 191B with glaucous wax remaining, between margin and center intermediate colors comprising nearest RHS 145A, nearest RHS 146D, nearest RHS 193B, and between RHS 191C and RHS 191D.

Petiole: Glabrous, deeply concavo-convex; stiff; mostly straight from base of plant to leaf base with little bending or arching, strong and slightly flexible; to about 54.5 cm long and 22 mm wide and 12 mm deep at base.

Petiole color: Adaxial and abaxial margin about 1 mm wide nearest RHS 158C, adaxial center nearest RHS 145B proximally and between RHS 145B and RHS 138B distally; abaxial center nearest RHS 145D with a thin band between the margin and center about 2 mm wide nearest 138A.

Veins: Parallel, lightly impressed adaxial, moderately bulging between veins; strongly costate and smooth abaxial side; about 14 to 15 pairs and one main center vein.

Veins color: Adaxial margin nearest RHS 157A, center variable nearest RHS 146D proximally and nearest RHS 194B distally; abaxial midrib nearest RHS 157B, main center veins nearest RHS 194D and marginal veins nearest 4D.

Flower description: Perfect; single; actinomorphic; funnelform; held outwardly to slightly drooping; mostly secund; persist for normal period, usually one day on plant or as cut flower; about 65 flowers per scape.

Flower period: Scapes remain effective with flowering beginning late June for about four to five weeks in Michigan.

Flower size: To about 56 mm long to exserted style; corolla to about 53 mm long and slightly flared to about 34 mm across at apex; distal bell portion 34 mm long and gradually tapering to corolla tube; corolla tube to about 19 mm long and 3.5 mm diameter toward base.

Fragrance: None detected.

Floral bracts: Subtending individual flowers; lanceolate to linear; narrowly acute apex, truncate clasping base, margin entire; glabrous adaxial and abaxial; to about 30 mm long and 16 mm across, decreasing in size distally; drying two to three days after flower dehisces.

Bract color: Adaxial and abaxial margins lightly blushed with nearest RHS N186C, adaxial nearest RHS 145D, abaxial center nearest RHS 145C.

Tepals: Two sets of three; lanceolate with acute apex and fused base.

*Inner set.*—56 mm long and 15 mm across slightly above fusion; fused in basal 30 mm and free in distal 26 mm; vitreous along 1 mm wide margin.

*Inner set color.*—Adaxial margin between RHS NN155D and RHS 85D to 4 mm wide in broadest portion, adaxial center between RHS 85A and RHS 85B distally and N87D proximally; abaxial free blade portion nearest RHS 85D and tube portion nearest RHS 85A.

*Outer tepal.*—56 mm long and 13 mm across slightly above fusion; fused in basal 30 mm and free in distal 26 mm; vitreous along 0.5 mm margin.

*Outer tepal color.*—Adaxial margin between RHS NN155D and RHS 85D to 2 mm wide in broadest portion, adaxial center between RHS 85A and RHS 85B distally and N87D proximally; abaxial free blade portion nearest RHS 85D and tube portion nearest RHS 85A.

Gynoecium: Single; tri-carpelled; 52.0 mm long.

*Style.*—Single; cylindrical; arcuate upward about 90° in distal 5 mm; about 48 mm long and 1 mm diameter; color RHS NN155C.

*Stigma.*—Flattened globose, micro-puberulent; about 1.5 mm across and 1 mm long; color nearest RHS NN155B distally and between RHS 145D and RHS 155C proximally.

*Ovary.*—Superior; ellipsoidal; rounded apex and truncate base; strongly longitudinally fluted; about 7 mm long and 3 mm diameter; color nearest RHS 145A.

Androecium: Six.

*Filaments.*—Cylindrical; glabrous; arcuate upward about 90° in distal 5 mm portion; about 48 mm long and 1 mm diameter; color nearest RHS NN155C distally and between RHS 155D and RHS NN155D proximally.

*Anthers.*—Oblong; dorsifixed, longitudinally dehiscent; about 4 mm long, 2 mm across, and 1 mm thick; color nearest RHS 200B and RHS N77A.

*Pollen.*—Smaller than 0.1 mm diameter; color nearest RHS 17B.

Flower bud: Clavate; with acute apex and fused tubular base; about 37 mm long in total and 9 mm wide in bulb portion, tube about 15 mm long and 3 mm diameter.

Flower bud color: Nearest RHS 85B.

Pedicel: Cylindrical, glabrous, slightly glaucous; outwardly to slightly drooping; mostly secund; to about 14 mm long and 2.0 rnm diameter.

Pedicel color: Between RHS 192D and RHS 196D with a light blush of nearest RHS N77C.

Peduncle: Cylindrical; usually one per mature division and five per plant; strongly glaucous; glabrous; very stiff, rigid; nearly upwardly with slightly arching distally; to about 86 cm long and about 10 mm diameter at base; flowering in upper 30 cm with about 65 flowers per scape.

Peduncle color: Distally nearest RHS 146A with a moderate blush of nearest RHS N186C, proximally between RHS 145A and RHS 145B without anthocyanin blushing.

Fruit: Non-fleshy, dehiscent, tri-loculicidal capsule; oblong to cylindrical with rounded apiculate apex and attenuate base; about 37 mm long and 8 mm diameter.

Fruit color: Nearest RHS 138A.

Seed: Typically about 33 to 42 per capsule under natural conditions; endospermic; flattened-ellipsoidal wing surrounding embryo at one end of ellipse; to about 12 mm long, 3 mm wide and 1.5 mm thick at embryo.

Seed color: Nearest RHS 202A.

Disease and pest tolerance and resistance: The new plant has not shown any resistance to pests, including *Odocoileus virginianus* and *Oryctotagus cuniculus*, and diseases common to *Hostas*. Growth: The plant grows best and shows best coloration with plenty of moisture, adequate drainage and light shade, but is able to tolerate some drought when mature. Hardiness: at least from USDA zone 3 through 9.

It is claimed:

1. A new and distinct ornamental *Hosta* plant named 'Gigantosaurus' as herein described and illustrated.

* * * * *